(12) United States Patent
Little et al.

(10) Patent No.: US 7,612,050 B2
(45) Date of Patent: *Nov. 3, 2009

(54) DRUG FOR THE TREATMENT OF OSTEONECROSIS AND FOR THE MANAGEMENT OF PATIENTS AT RISK OF DEVELOPING OSTEONECROSIS

(75) Inventors: David Graham Little, Westmead (AU); Nicholas Charles Smith, Westmead (AU)

(73) Assignee: The Royal Alexandra Hospital for Children, Westmead, NSW (AU)

( * ) Notice: Subject to any disclaimer, the term of this patent is extended or adjusted under 35 U.S.C. 154(b) by 0 days.

This patent is subject to a terminal disclaimer.

(21) Appl. No.: 12/191,264

(22) Filed: Aug. 13, 2008

(65) Prior Publication Data

US 2009/0005347 A1    Jan. 1, 2009

Related U.S. Application Data (63) Continuation of application No. 10/470,924, filed as application No. PCT/AU01/01616 on Dec. 13, 2001, now Pat. No. 7,425,549.

(30) Foreign Application Priority Data

Feb. 6, 2001   (AU) ..................... PR2907
Apr. 3, 2001   (AU) ..................... PR4187
Jul. 27, 2001  (AU) ..................... PR6654

(51) Int. Cl.
*A61K 31/675*   (2006.01)

(52) U.S. Cl. ............... 514/89; 514/2; 514/7; 514/8

(58) Field of Classification Search ................ None
See application file for complete search history.

(56) References Cited

U.S. PATENT DOCUMENTS

| | | | |
|---|---|---|---|
| 5,755,809 A * | 5/1998 | Cohen et al. | 623/23.35 |
| 5,843,678 A * | 12/1998 | Boyle | 435/7.1 |
| 6,316,408 B1 | 11/2001 | Boyle | |
| 7,425,549 B2 * | 9/2008 | Little et al. | 514/89 |

FOREIGN PATENT DOCUMENTS

WO    WO0243738    6/2002

OTHER PUBLICATIONS

Fulfaro et al., 1998, Pain 78:157-169.*
Podwomy et al., 1999, J. Rheumatol. 26:1972-1982.*

* cited by examiner

*Primary Examiner*—Elizabeth C Kemmerer
(74) *Attorney, Agent, or Firm*—Carol L. Francis; Bozicevic, Field & Francis, LLP (57) ABSTRACT

A bisphosphonate for the treatment of osteonecrosis and/or osteonecrosis dissecans. The drug may further he used to prevent the onset of osteonecrosis and/or osetonecrosis dissecans and any complications associated with both diseases.

28 Claims, 7 Drawing Sheets

DRUG FOR THE TREATMENT OF OSTEONECROSIS AND FOR THE MANAGEMENT OF PATIENTS AT RISK OF DEVELOPING OSTEONECROSIS

This application is a continuation of application Ser. No. 10/470,924, filed Dec. 19, 2003, issued as U.S. Pat. No. 7,425,549 on Sep. 16, 2008, which is a §371 national phase application of international application serial no. PCT/AU01/01616, filed Dec. 13, 2001, which application claims priority benefit to each of Australian application no. PR 2907, filed Feb. 6, 2001, Australian application no. PR 4187, filed Apr. 3, 2001, and Australian application no. PR 6654, filed Jul. 27, 2001.

FIELD OF THE INVENTION

The present invention relates to new indications for a certain class of drugs. More specifically, the present invention relates to the use of bisphosphonates in the treatment of osteonecrosis and related disorders such as osteochondritis dissecans. In a further disclosure, the invention relates to the use of bisphosphonates in the management of patients at risk of developing osteonecrosis.

BACKGROUND OF THE INVENTION

Osteonecrosis is a distinct clinical and pathological entity, with many different causes and differing pathogeneses. Although much has been written about the disorder, all the factors in the aetiology and pathogenesis are not known at this time. Osteonecrosis can affect an area spontaneously in adults and children (Perthes disease), or result from such disease processes as alcoholism, exposure to glucocorticoids and or cytotoxic drugs, exposure to a hyperbaric environment (caisson disease)[i], fracture, infection, haematological disease, to name some examples. No proven pharmacological agent is currently available for the treatment of osteonecrosis.

The consequences of this disorder are severe as osteonecrosis usually affects the function of a joint and most commonly the hip joint. If the hip joint is affected, the femoral head is susceptible to collapse, leading to pain, stiffness and long-term disability. The affected joint is further susceptible to deformity and osteoarthritis. Osteonecrosis having unknown aetiology affects a significant percentage of the population including children. Particularly, Perthes disease (Legg-Calve-Perthes disease) is common, with an incidence of 8.5 to 21 per 100,000 children per annum[ii,iii,iv,v]. The aetiology of Perthes disease remains unknown, but the common final pathway of the majority of theories suggest a vascular insult resulting in a period of relative ischaemia and osteonecrosis, leading to resorption and collapse of the necrotic epiphysis.[vi,vii,viii]

Perthes disease is well known to lead to osteoarthritis. By age 56, 40% of affected patients in one study underwent total hip replacement surgery. Subchondral bony collapse proceeds as the femoral head becomes weaker and more osteoporotic. There is currently no known effective medical treatment for Perthes disease. Mechanical treatments such as bracing have been largely discarded, as they have not proven to alter the natural history of the disorder[ix,x]. Current opinion dictates that if a child's hip reaches a certain degree of deformity, an operation is indicated to place the femoral head in a better position in the joint in an attempt to produce a more spherical hip, and thus better long term outcome. Few of the surgical options are designed to prevent collapse and are aimed at salvaging the situation once collapse and deformity of the hip have ensued. Current surgical therapies meet with limited or mixed success[xi,xii,xiii].

There are other situations where osteonecrosis of the femoral head is also manifest in childhood. Children with malignant disease are particularly prone to developing osteonecrosis. Mattano et al showed that of 1,409 children with acute lymphoblastic leukaemia (ALL) the 3-year life-table incidence of developing osteonecrosis is 9.3%[xiv]. In that study symptoms of pain and/or immobility were chronic in 84% of patients, with 24% having undergone an orthopaedic procedure and an additional 15% considered candidates for surgery in the future. In a prospective MRI study of 24 children with acute lymphoblastic leukaemia, Ojala et al documented osteonecrosis in 38%[xv].

Osteonecrosis also occurs in patients who are recovering from bone marrow, kidney, lung and liver transplantation[xvi,xvii,xviii,xix]. Children who sustain a fracture of the neck of the femur can also go on to suffer from osteonecrosis of the femoral head, as can children with slipped upper femoral epiphysis. The outcome in patients is often poor if they develop avascular necrosis[xx]. In a recent study of femoral neck fracture in children, avascular necrosis occurred in 40%[xxi].

In adult patients, progressive collapse of the bone and cartilage of the joint ensues, often coinciding with a subchondral fracture. In a prospective study of osteonecrosis of the femoral head, Ito et al found that 64% were symptomatic at mean six-year follow-up[xxii]. In older persons, progressive collapse and deformity of the femoral head can be rapid, with 66% of patients progressing to collapse within a short period, and 22% having rapid resorption and destruction of the femoral head[xxiii]. For these elderly patients, exposure to total hip arthroplasty surgery to resolve the subsequent pain and immobility of their hip poses considerable risk.

Surgical solutions for osteonecrosis include core decompression to reduce the intraosseous pressure and increase new blood supply; bone grafting, either through the core decompression or through the joint (trapdoor procedure); vascularised bone and/or tissue transplantation; and redirectional osteotomy of the affected segment away from load. Containment treatment in Perthes disease, either non-operative or operative, in an attempt to reshape the collapsed femoral head, is well described. The use of an external fixator or brace to unload the joint and prevent collapse of the affected part is also well described. Surgical treatment of the related disease osteochondritis dissecans usually involves stabilising a fragment of subchondral bone which has become detached from the adjacent bone with a fixation device, with or without bone grafting and drilling of the bone. Sometimes excision of the fragment is required.

Recent techniques involve the treatment of osteonecrosis with hyperbaric oxygen, however, some authors have theorised that caisson disease may be due to hyperbaric oxygen rather than nitrogen[xxiv]. Indeed, in a recent study of 20 children presenting with osteonecrosis in the course of cytotoxic chemotherapy, no difference was found in sequential MRI in the group treated with hyperbaric oxygen than in control subjects[xxv].

Despite the availability of such treatments, the prognosis for diseases such as osteonecrosis and osteochondritis dissecans is poor. Once the condition is identified, collapse of the affected bone continues over months to years, leading to deformity and osteoarthritis of the relevant joint.

Both conditions can lead to immobility of the patient and the cost to the individual and community is great particularly as osteonecrosis and particularly osteochondritis dissecans often occur in young, healthy patients.

Total joint replacement, often at a young age—with its attendant complications and short life span, is often required to resolve the pain and suffering of such individuals. A pharmacological therapy, therefore, offers these patients enormous benefits.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

SUMMARY OF THE INVENTION

In a first aspect, the present invention consists in a drug selected from a group consisting of at least one bisphosphonate when used for the treatment of osteonecrosis.

In a second aspect, the present invention consists in a drug selected from a group consisting of at least one bisphosphonate when used for the treatment of osteochondritis dissecans.

In a third aspect, the invention consists in a method of treating a patient with osteonecrosis and/or osteochondritis dissecans, the method including the step of administering to the patient a drug selected from a group consisting of at least one bisphosphonate.

In a fourth aspect, the invention consists in a method of preventing osteonecrosis and/or osteochondritis dissecans and any complications associated with said diseases in a patient at risk of either of the diseases, the method including the step of administering to the patient a drug selected from the group consisting of at least one bisphosphonate.

In a fifth aspect, the invention consists in the use of a drug selected from a group consisting of at least one bisphosphonate for the manufacture of a medicament for the treatment of osteonecrosis.

In a sixth aspect, the invention consists in the use of a drug selected from a group consisting of at least one bisphosphonate for the manufacture of a medicament for the treatment of osteochondritis dissecans.

In a seventh aspect, the invention consists in the use of a drug selected from the group consisting of at least one bisphosphonate for the manufacture of a medicament suitable for prophylactic administration to a patient at risk of developing osteonecrosis and/or osteochondritis dissecans.

In an eighth aspect, the present invention consists in a drug selected from the group consisting of at least one bisphosphonate when used for the prevention of cartilage destruction or chondrolysis associated with osteonecrosis and/or osteochondritis dissecans.

In a ninth aspect, the present invention consists in a method of preventing cartilage destruction or chondrolysis associated with osteonecrosis and/or osteochondritis dissecans, the method including the step of administering to a patient a drug selected from the group consisting of at least one bisphosphonate.

The selected bisphosphonate preferably acts to at least lessen or prevent the severity of deformity and/or collapse of bone and cartilage and permit new bone formation in the patient.

Where the drug is administered prophylactically to a patient at risk of either osteonecrosis or osteochondritis dissecans, such prophylactic administration preferably has the effect of creating a depot of therapeutically effective bisphosphonate within the body of the patient thereby minimising collapse and deformity of the bone and encouraging new bone formation, and maintenance of bone structure, should osteonecrosis occur.

In a preferred embodiment, the drug is given intravenously. Alternatively, the drug may be given orally. Further, the drug may be administered subcutaneously, intramuscularly, transdermally, topically or by any other route whence it can produce its therapeutic effect. It is further envisaged that the drug is administered locally to a target site. For example, the drug may be administered locally during a surgical procedure for osteonecrosis.

In an embodiment wherein the drug is administered locally, as part of a procedure, the drug may be administered by direct application to bone surfaces, or as part of a local delivery system. The local delivery system may take the form of a bone graft substitute or extender, or autogenous or allogenic bone graft. The bone graft substitute or extender may contain calcium sulphate, calcium carbonate, tricalcium phosphate, hydroxyapatite, or other calcium containing compounds, alone or in any combination. The bone graft substitute, extender, autograft or allograft may also contain, in addition to being admixed with an effective amount of bisphosphonate, a carrier medium such as collagen, gelatine, glycerol, propylene glycol, resin, polyglycolic acid (PGA), poly-l lactic acid (PLLA), poly dl lactic acid (PLLA), porous silicon, or any other resorbable biocompatible medium, either in the form of injectable liquid, gel, putty or cement or in the form of mouldable liquid, cement, putty, gel, flexible sheets, mesh or sponge or other readily applicable method. It may also include any combination of above and any binding agent. The bisphosphonate and the carrier alone may also be used for local delivery. Further systemic doses may or may not be advantageous in addition to the initial local or systemic dose.

The carrier may contain nutrients required by cells involved in bone formation or other cells and is preferably resorbable. The carrier may further contain gene products known to be implicated in bone healing. Examples of suitable gene products include, but are not limited to, Bone Morphogenetic Protein 7 (OP-1), BMP-2 and -4, other bone morphogenetic proteins, transforming growth factor beta, fibroblast growth factor (basic or acidic), insulin-like growth factor −1 or −2, osteocalcin, or other known biologically active proteins, polypeptides, or gene products. Such methodology is likely to have a beneficial synergistic effect—the bisphosphonate stabilising the skeletal structure and the growth factors potentially stimulating increased vascularization and new bone formation over bisphosphonate administration alone. Likewise the combination is likely to be more effective than these growth factor gene products alone, as new bone formed in response to the growth factors will be better maintained by use of a bisphosphonate.

The carrier medium may also contain blood products containing growth factors or cells, "buffy coat" (for example AGF™), bone marrow aspirate or cultured osteoblastic cells or precursors, or multipotential stem cells. The carrier may also contain cells transfected with bone formation genes, for example via an adenoviral vector, such that they overexpress genes implicated in bone healing, leading to increased bone formation. Again such combination therapy is likely to be synergistic, the bisphosphonate stabilising the skeletal structure and the cells stimulating increased new bone formation over bisphosphonate administration alone.

A number of combination of cells, gene product growth factors, nutrients, carrier medium and bone graft substitute may prove efficacious when admixed with at least one bisphosphonate.

In another embodiment, the drug is zoledronic acid (zoledronate) {1-hydroxy-2-[(1H-imidazol-1-yl)ethylidine] bisphosphonic acid}. Alternatively, the drug may be pamidronate {3-amino-1-hydroxypropylidene bisphosphonic acid}, alendronate {4-amino-1-hydroxybutylidene bisphosphonic acid}, etidronate {1-hydroxyethylidene bisphosphonic acid}, clodronate {dichloromethylene bisphosphonic acid}, risedronate {2-(3-pyridinyl)-1-hydroxyethylidene bisphosphonic acid}, tiludronate {chloro-4-phenylthiomethylidene bisphosphonic acid}, ibandronate {1-hydroxy-3(methylpentylamino)-propylidene bisphosphonic acid}, incadronate {cycloheptyl-amino-methylene bisphosphonic acid}, minodronate {[1-hydroxy-2-(imidazo[1,2-a]pyridin-3-yl)ethylidene]bisphosphonic acid}, olpadronate {(3-dimethylamino-1-hydroxypropylidene) bisphosphonic acid}, neridronate (6-amino-1-hydroxyhexylidene-1,1-bisphosphonic acid), EB-1053 1-hydroxy-3-(1-pyrrolidinyl)-propylidene-1,1-bisphosphonic acid, or any other therapeutically effective bisphosphonate or pharmaceutically acceptable salts or esters thereof.

In one embodiment, the osteonecrosis or osteochondritis dissecans affects the femoral head, distal femur, proximal tibia, talus, navicular or other tarsal bone, metatarsal head, humeral head or proximal humerus, capitellum or distal humerus, radial head, scaphoid, lunate or other carpal bone. It is envisaged, however, that the disease may affect any other bone or joint within the body of a patient.

In a further embodiment, the osteonecrosis presents in a child diagnosed with Perthes disease (Legg-Calve-Perthes disease).

In another embodiment, the osteonecrosis or osteochondritis may be of unknown cause.

In a further embodiment, the osteonecrosis or osteochondritis dissecans may develop secondary to a disease process. By way of example only, the osteonecrosis or osteochondritis dissecans may be secondary to disease such as Gaucher's disease, sickle cell disease or other haematological disorder, renal failure, liver failure, endocrine disorder, HIV and associated syndromes, leukaemia or other malignancy, primary bone dysplasia, connective tissue disorder, autoimmune disorder, or immunosuppression disorder.

The osteonecrosis or osteochondritis dissecans may develop following exposure to substances known to be of high risk in causing osteonecrosis, including but not limited to corticosteroids (glucocorticoids), cyclosporin or other immune suppressant medications, cytotoxic drugs for malignancy or forms of rheumatoid arthritis, illicit substance abuse, alcohol abuse, and/or cigarette smoking.

The osteonecrosis or osteochondritis dissecans may develop following a bone marrow transplant or organ transplant.

In another embodiment, the osteonecrosis or osteochondritis dissecans may be related to a trauma such as a fracture. The fracture may be of the femoral head, neck or intertrochanteric femoral fracture, fracture of the head or neck of the radius, capitellum of the humerus, fracture of the talus or other tarsal bone, fracture of the humeral head, neck or subcapital region in the shoulder, fracture of the scaphoid, lunate or other carpal bone. Alternatively the fracture may be in some other bone.

The osteonecrosis or osteochondritis dissecans may be related to an injury that is not a fracture, for example, a dislocation or subluxation.

The drug may be administered to a patient perioperatively for osteonecrosis or osteochondritis dissecans. The surgery may involve core decompression, bone graft, vascularised bone or tissue graft or transfer, "trapdoor" bone grafting procedure, osteoplasty or chondroplasty, osteotomy, or internal or external fixation.

In cases wherein the drug selected from the group consisting of at least one bisphosphonate is administered prophylactically, the drug may be administered to a patient who is known to have previously suffered from osteonecrosis at one site, and who is therefore at high risk of developing osteonecrosis at another site. In this case, the known osteonecrosis may involve the femoral head, distal femur, proximal tibia, talus or other tarsal bone, metatarsal head, humeral head or proximal humerus, capitellum or distal humerus, radial head, scaphoid, lunate or other carpal bone.

In a further embodiment, the drug may be administered prophylactically to patient who has suffered a fracture wherein there is a high risk of the fracture leading to osteonecrosis. The fracture may be of the femoral head, neck or intertrochanteric femoral fracture, a slipped capital femoral epiphysis or other epiphysis, fracture of the head or neck of the radius, capitellum of the humerus, fracture of the talus or other tarsal bone, fracture of the humeral head, neck or subcapital region in the shoulder, fracture of the scaphoid, lunate or other carpal bone. Alternatively, prophylactic treatment may be commenced on a patient who has suffered an injury that is not a fracture, for example, a dislocation or subluxation, wherein the injury has a risk of leading to osteonecrosis, for example, traumatic hip dislocation and traumatic shoulder dislocation.

In yet another embodiment, the drug may be administered prophylactically to a patient who is to undergo, is undergoing or has recently undergone, an operation known to be associated with osteonecrosis. In this embodiment, the operation may involve reduction of a congenital or developmental dislocation of the hip, an osteotomy near any joint, an osteoplasty, core decompression or bone graft, vascularized bone or soft tissue transfer, "trapdoor" bone grafting procedure for the treatment of osteonecrosis.

A further indication for prophylactic treatment may be in cases of osteonecrosis or osteochondritis dissecans secondary to a disease process such as Gaucher's disease, sickle cell disease or other haematological disorder, renal failure, liver failure, endocrine disorder, HIV and associated syndromes, leukaemia or other malignancy, primary bone dysplasia, connective tissue disorder, autoimmune disorder, or immunosuppression disorder.

The patient that is the subject of prophylactic treatment may have been exposed to substances known to be of high risk in causing osteonecrosis including but not limited to corticosteroids (glucocorticoids), cyclosporin or other immune suppressants, cytotoxic drugs for malignancy or forms of rheumatoid arthritis, illicit substance abuse, alcohol abuse, and/or cigarette smoking.

In another embodiment, the patient may be at high risk of developing osteonecrosis or osteochondritis dissecans following a bone marrow transplant or organ transplant.

In a further embodiment, the drug of the present invention may be administered concurrently with a radiotherapy regime.

The bisphosphonate may be zoledronic acid (zoledronate), or any pharmaceutically acceptable salt or ester thereof. Preferably, the zoledronic acid is administered parenterally and preferably in a dose from about 0.25 mg to about 12 mg in an adult patient or about 0.005 mg/kg to about 0.5 mg/kg in a child, approximately every three months. However, it is envisaged that the zoledronic acid may be administered four-weekly, six-weekly or every two months. Further, the zoledronic acid may be administered as a single dose and further doses administered if required.

In another embodiment, the zoledronic acid may be administered parenterally in a dose of about 2 mg, about 4 mg, about 6 mg or about 8 mg for an adult patient or about 0.025 mg/kg, about 0.05 mg/kg, about 0.075 mg/kg or about 0.1 mg/kg in a child, approximately every three months. The zoledronic acid may be administered parenterally in a dose of about 2 mg, about 4 mg, about 6 mg or about 8 mg for an adult patient or about 0.025 mg/kg, about 0.05 mg/kg, about 0.075 mg/kg or about 0.1 mg/kg in a child, approximately every six months. In a still further embodiment, the zoledronic acid may be administered parenterally in a dose of about 2 mg, about 4 mg, about 6 mg or about 8 mg for an adult patient or about 0.025 mg/kg, about 0.05 mg/kg, about 0.075 mg/kg or about 0.1 mg/kg in a child, approximately every twelve months. In a further embodiment, the zoledronic acid may be administered parenterally in a dose of about 2 mg, about 4 mg, about 6 mg or about 8 mg for an adult patient or about 0.025 mg/kg, about 0.05 mg/kg, about 0.075 mg/kg or about 0.1 mg/kg in a child, as a single dose. Alternatively, the zoledronic acid may be given orally.

In another embodiment, the bisphosphonate is pamidronate or any pharmaceutically acceptable salt or ester thereof. Preferably, the pamidronate is administered parenterally and preferably in a dose from about 15 to about 90 mg approximately every one to three months in an adult patient or 0.25 mg/kg to 3.0 mg/kg every one to three months in a child. In a further embodiment the pamidronate may be administered parenterally in a dose of about 15 mg, about 30 mg, about 60 mg or about 90 mg every one to three months in an adult patient or 0.25 mg/kg, about 0.5 mg/kg, about 1.0 mg/kg, about 2.0 mg/kg or about 3.0 mg/kg every one to three months in a child. In a still further embodiment, pamidronate is administered parenterally in a dose of about 15 mg, about 30 mg about 60 mg or about 90 mg approximately every six months in an adult patient or 0.25 mg/kg, about 0.5 mg/kg, about 1.0 mg/kg, about 2.0 mg/kg or about 3.0 mg/kg approximately every six months in a child. In yet another embodiment, pamidronate is administered parenterally in a dose of about 15 mg, about 30 mg, about 60 mg or about 90 mg approximately every twelve months in an adult patient or 0.25 mg/kg, about 0.5 mg/kg, about 1.0 mg/kg, about 2.0 mg/kg or about 3.0 mg/kg approximately every twelve months in a child. In still another embodiment, pamidronate is administered parenterally in a dose of about 15 mg, about 30 mg, about 60 mg, or about 90 mg in an adult patient or 0.25 mg/kg, about 0.5 mg/kg, about 1.0 mg/kg, about 2.0 mg/kg or about 3.0 mg/kg in a child, as a single dose.

In another embodiment, the bisphosphonate is alendronate or any pharmaceutically acceptable salt or ester thereof. Preferably, the alendronate is administered orally and preferably in a dose from about 2.5 mg to about 50 mg per day or about 10 mg to about 300 mg per week for an adult patient. In a child the preferable oral dose is from about 0.05 mg/kg to 1.0 mg/kg per day or about 0.2 mg/kg to 6.0 mg/kg per week. The alendronate may be administered orally in a dose of about 5 mg, about 10 mg, about 20 mg or about 40 mg per day or about 35 mg, about 70 mg about 140 mg or about 280 mg per week for an adult. For a child, the alendronate may be administered orally in a dose of about 0.1 mg/kg, about 0.2 mg/kg, about 0.4 mg/kg, or about 0.8 mg/kg per day, or about 0.8 mg/kg, about 1.5 mg/kg, about 3.0 mg/kg or about 5.0 mg/kg per week. Alternatively, the alendronate is administered parenterally and preferably in a dose from about 0.25 mg to about 30 mg approximately every one to three months, or as a single dose.

In a further embodiment, the bisphosphonate is risedronate or any pharmaceutically acceptable salt or ester thereof. Preferably, the risedronate is administered orally and preferably in a dose from about 2.5 mg to about 60 mg per day or about 10 mg to about 300 mg per week in an adult patient or about 0.05 mg/kg to about 1.0 mg/kg per day or about 0.25 mg/kg to about 7.0 mg/kg in a child. The risedronate may be administered orally in a dose of about 2.5 mg, about 5 mg, about 10 mg or about 30 mg per day, or about 15 mg, about 30 mg, about 60 mg, or about 210 mg per week in an adult patient or, for a child, about 0.05 mg/kg, about 0.1 mg/kg, about 0.2 mg/kg, about 0.5 mg/kg per day, or about 0.25 mg/kg, or about 0.5 mg/kg, about 1.0 mg/kg, or about 2.5 mg/kg per week. Alternatively, the Risedronate may be administered intravenously.

In a further embodiment, the bisphosphonate is ibandronate or any pharmaceutically acceptable salt or ester thereof. Preferably, the ibandronate is administered parenterally and preferably in a dose from about 0.25 mg to about 30 mg, and more preferably in a dose of about 2 mg to 10 mg approximately every one to three months, or as a single dose.

In another embodiment the ibandronate is given orally in a dose of about 2.5 mg, about 5 mg, about 10 mg or about 30 mg per day, or about 15 mg, about 30 mg, about 60 mg, or about 210 mg per week in an adult patient or, for a child, about 0.05 mg/kg, about 0.1 mg/kg, about 0.2 mg/kg, about 0.5 mg/kg per day, or about 0.25 mg/kg, or about 0.5 mg/kg, about 1.0 mg/kg, or about 2.5 mg/kg per week.

In yet another embodiment, the bisphosphonate is incadronate or any pharmaceutically acceptable salt or ester thereof. Preferably, the incadronate is administered parenterally and preferably in a dose from about 0.25 mg to about 30 mg, more preferably about 10 mg in an adult patient or, for a child, from about 0.005 mg/kg to 0.6 mg/kg, more preferably about 0.025 mg/kg to 0.25 mg/kg approximately every one to three months, or as a single dose.

In another embodiment the incadronate is given orally in a dose of about 2.5 mg, about 5 mg, about 10 mg or about 30 mg per day, or about 15 mg, about 30 mg, about 60 mg, or about 210 mg per week in an adult patient or, for a child, about 0.05 mg/kg, about 0.1 mg/kg, about 0.2 mg/kg, about 0.5 mg/kg per day, or about 0.25 mg/kg, or about 0.5 mg/kg, about 1.0 mg/kg, or about 2.5 mg/kg per week.

In still another embodiment, the bisphosphonate is minodronate or any pharmaceutically acceptable salt or ester thereof. Preferably, the minodronate is administered 0.25 mg to about 30 mg approximately every one to three months, or as a single dose. More preferably, the minodronate is administered parenterally and preferably in a dose from about 0.25 mg to about 12 mg in an adult patient or about 0.005 mg/kg to about 0.5 mg/kg in a child, approximately every three months. In another embodiment, the minodronate may be administered parenterally in a dose of about 2 mg, about 4 mg, about 6 mg or about 8 mg for an adult patient or about 0.025 mg/kg, about 0.05 mg/kg, about 0.075 mg/kg or about 0.1 mg/kg in a child, approximately every three months. The minodronate may be administered parenterally in a dose of about 2 mg, about 4 mg, about 6 mg or about 8 mg for an adult patient or about 0.025 mg/kg, about 0.05 mg/kg, about 0.075 mg/kg or about 0.1 mg/kg in a child, approximately every six months. In a still further embodiment, the minodronate may be administered parenterally in a dose of about 2 mg, about 4 mg, about 6 mg or about 8 mg for an adult patient or about 0.025 mg/kg, about 0.05 mg/kg, about 0.075 mg/kg or about 0.1 mg/kg in a child, approximately every twelve months. In a further embodiment, the minodronate may be administered parenterally in a dose of about 2 mg, about 4 mg, about 6 mg or about 8 mg for an adult patient or about 0.025 mg/kg, about 0.05 mg/kg, about 0.075 mg/kg or about 0.1 mg/kg in a child, as a single dose. Alternatively, the minodronate may be given orally.

In another embodiment, the bisphosphonate is clodronate or any pharmaceutically acceptable salt or ester thereof. The clodronate may be given orally in a dose range of about 400 mg to 2400 mg per day in an adult or, for a child, 50 mg/kg to 250 mg/kg or administered intravenously in dose ranges from 150 mg to 300 mg or, for a child, 1 mg/kg to 5 mg/kg, repeated daily for 2 to 5 days, and repeated as necessary, possibly every one to six months.

In another embodiment, the bisphosphonate is etidronate or any pharmaceutically acceptable salt or ester thereof. The etidronate may be given orally in a dose range of about 100 to 400 mg (5 to 20 mg/kg per day) or, for a child, 5 to 20 mg/kg per day.

In another embodiment, the bisphosphonate is tiludronate or any pharmaceutically acceptable salt or ester thereof. The tiludronate may be given orally in a dose range of about 400 mg per day in an adult or, for a child, 5 to 20 mg/kg per day.

In another embodiment, the bisphosphonate is olpadronate or any pharmaceutically acceptable salt or ester thereof. The olpadronate may be given orally in a dose range of about 50-400 mg per day in an adult or, for a child, 1 mg/kg to 10 mg/kg or administered intravenously in dose ranges from 1 mg to 20 mg or, for a child, 0.1 mg/kg to 0.5 mg/kg, every one to three months.

In still another embodiment, the bisphosphonate is neridronate or any pharmaceutically acceptable salt or ester thereof. In another embodiment the neridronate is given parenterally in a dose range from 10 mg to 100 mg in an adult, or for a child, 0.1 to 2 mg/kg intravenously every one to three months.

In another embodiment the drug is EB-1053.

BRIEF DESCRIPTION OF THE DRAWINGS

By way of example only, a preferred embodiment of the invention is described with reference to the accompanying figures.

PREFERRED EMBODIMENT OF THE INVENTION

Figure 1:
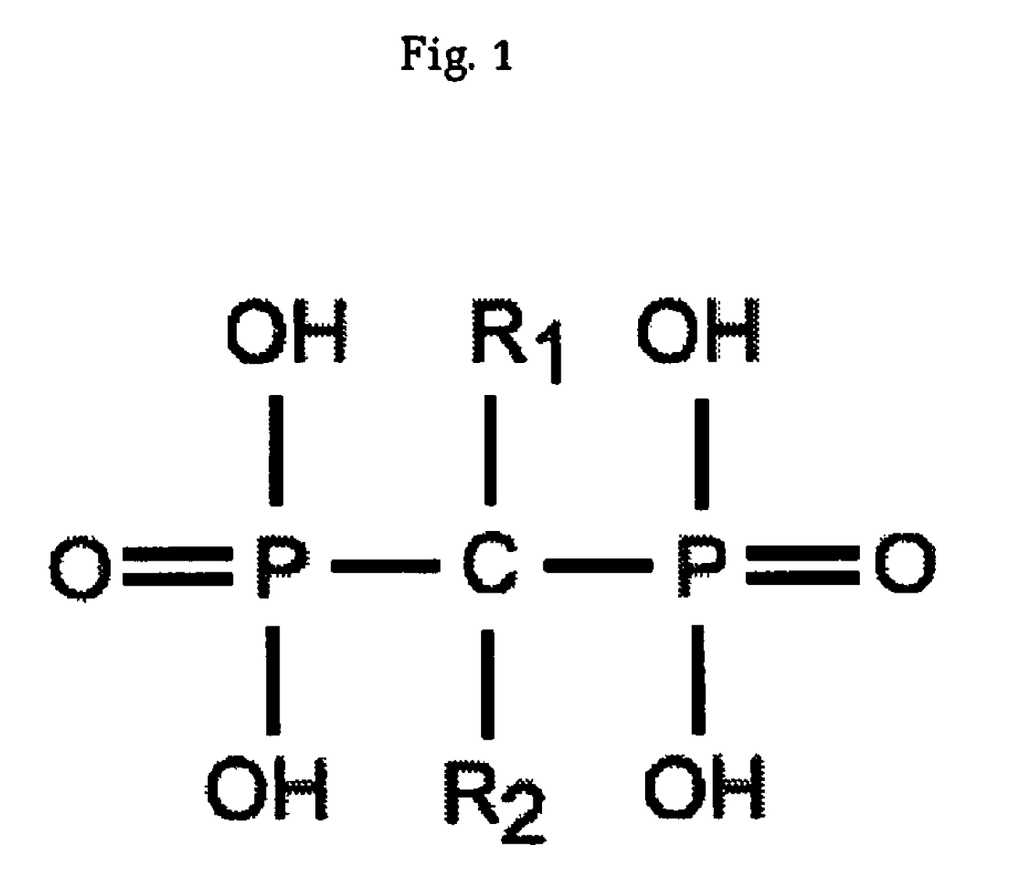
FIG. 1 is a generic formula for one class of bisphosphonates.

The invention relates to the use of a bisphosphonate with the following formula depicted in FIG. 1 wherein $R_1$ and $R_2$ are varied to give various potencies and other properties to the bisphosphonate.

The present invention relates to a novel pharmacological treatment for osteonecrosis, including osteonecrosis affecting bone and cartilage adjacent to a joint. By administering a therapeutically effective dose of at least one bisphosphonate, such as zoledronic acid, the collapse of the necrotic bone can be slowed due to decreased osteoclast activity, while increases in the mineralisation of new bone may speed up the reparative process with new bone of improved mechanical integrity, thereby reducing the magnitude of any collapse of the affected bone and cartilage. This minimises the risk of deformity of the joint or bone and, further, reduces the risk of pain and the development of osteoarthritis.

It is known that bisphosphonates remain therapeutically effective over long periods. As such, when the blood supply returns to a necrotic site, as evidenced by bone scan images of affected bone, the necrotic bone commences uptake any circulating bisphosphonate. The bisphosphonates protective and reparative action then commences, so delaying collapse of the necrotic bone while highly mineralised new bone is laid down in response to bisphosphonate therapy. The highly mineralised new bone improves the mechanical integrity of the affected joint.

Other studies have suggested that zoledronic acid inhibits angiogenesis in the dose range used in this study[xxvi] and as such, would not be expected to be a useful adjunct in the treatment of osteonecrosis. Our previous results showing that zoledronic acid administration leads to increased callus formation, mineralisation and strength in distraction osteogenesis in rabbits were not consistent with these observations[xxvii]. This is based on the understanding that angiogenesis is a critical factor in bone formation. The hypotheses used in designing this experiment were based on the knowledge that bisphosphonate therapy can lead to both anti-resorptive and pro-osteoblastic effects. Positive effects of bisphosphonates on osteoblasts are now widely known, they do not act on osteoclasts alone[xxviii,xxix]. As such bisphosphonate therapy may provide solutions for fractures prone to osteonecrosis, such in the femoral neck, talar neck or scaphoid, increasing new bone formation and preventing collapse from osteonecrosis.

Figure 2:
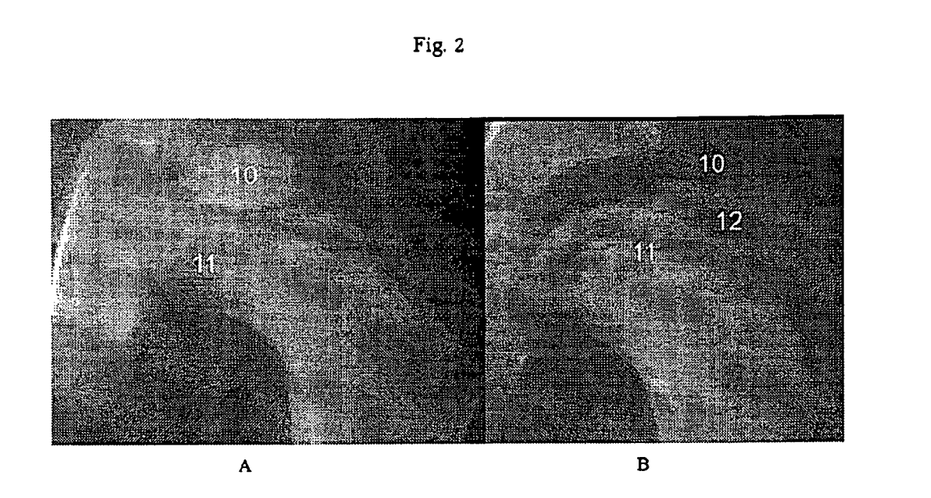
FIGS. 2A and 2B are radiographs of patients diagnosed with Perthes disease.

An example is given in FIG. 2. Radiograph (A) shows the hip joint of a 7 year old boy diagnosed with Perthes disease six months prior to the taking of the X-ray. Radiograph (B) shows the hip joint of a second boy diagnosed with Perthes disease twelve months prior to the taking of the X-ray. One can see the following typical features underlying the progression of Perthes disease. The epiphysis (growing femoral head) 10 is clearly necrotic. The highly mineralised bone in the necrotic epiphysis is being resorbed in response to various endogenous mediators, such that its mechanical integrity is breached, and it is collapsing. In concert with necrotic bone resorption there is resorption of the metaphyseal bone 11 (the bone internal to the shaft and particularly the region which abuts with the epiphyseal or growth plate), presumably by the same mediators. This removes structural support for the growth plate 12, which soon collapses and becomes disorganised, limiting the growth and recovery potential of the femoral head 10. New bone formation in the lateral aspect of the femoral head 10 is of poor quality, with little mechanical integrity. It is slowly extruded from the joint over time leaving a saddle shape to the femoral head 10.

Application of a therapeutically effective amount of bisphosphonate will slow the resorption and collapse of the necrotic bone, limit the resorption of the metaphyseal bone and promote increased mineral content in the new bone forming in the lateral portion of the epiphysis. By preventing collapse of the necrotic bone and increasing the mechanical integrity of the new bone, a more spherical shape of the femoral head will be maintained. As prognosis in Perthes disease is directly referable to femoral head sphericity[xxx], such application of a therapeutically effective dose of a bisphosphonate is likely to provide significantly improved outcomes for patients with Perthes disease.

EXAMPLE 1

The following example outlines the process by which the effects of bisphosphonates on a necrotic bone may be observed.

A model of traumatic osteonecrosis was utilised in 24 female 14-week-old Wistar rats. The animals were followed for six weeks after an operation designed to disrupt the blood supply to the femoral head. The six week time point was chosen as a time point when femoral head collapse is known to have occurred in this model[1]. Animal ethics approval was received.

Rats were randomised in lots of 4 into three groups according to the schedule below. Controls receive only saline (S) injections via a subcutaneous route. Post-treated animals received saline only pre-operatively, but zoledronic acid (ZA) (Novartis) 0.1 mg/kg, from commercial stock, was administered by subcutaneous injection post-operatively at 1 and 4 weeks. Pre and Post-treated animals received zoledronic acid 0.1 mg/kg at all three time points.

The same operation was performed on each rat at time zero. All animals were weighed accurately before anaesthesia. Animals were kept warm during surgery and recovery. Anaesthesia was induced with a mixture of Ketamine 75 mg/kg and Xylazine 10 mg/kg. Drugs were mixed in the same syringe just prior to administration and given 0.2 mL per 100 g BW IM. Induction occurred within 5-10 minutes.

After sterile preparation and shaving of the right lower extremity, an open approach was made to the hip joint. The capsule was opened, and the right femoral head was dislocated from the acetabulum. The ligamentum teres divided, disrupting any blood supply from that source. The entire femoral neck was denuded of soft tissue by polishing with a vicryl suture. This disrupted the lateral epiphyseal artery and any other vessels supplying the head via the femoral neck.

Animals were allowed rat pellet and water ad libitum and caged in groups of 4.

Dual fluorescent labels were applied at weeks 4 and 5: at week 4 demeclocycline 30 mg/kg was administered intraperitoneally, and at week 5 calcein 20 mg/kg was administered intraperitoneally. One hour prior to culling 70 MBq Tc99 MDP was administered subcutaneously to allow bone scintigraphy to be performed on harvested specimens.

After culling, right and left proximal femora were harvested and fixed in 4% paraformaldehyde. Radiographs were taken in pairs on high quality film with a Faxitron Shielded Cabinet X-Ray System (Hewlett Packard, McMinnville, Oreg.). X-ray images were digitised and analysed using Bioquant image analysis system (R&M Biometrics Inc., Nashville, Tenn.) connected to a digitizing tablet (GTCO Cal-Comp, Inc., Columbia, Md.). Bone area, height and width of the femoral head were recorded and compared to the contralateral side. Scintigraphy scans were taken using 4 mm aperture pinholes. BMD and BMC were measured with a pDEXA Sabre scanner (Norland, Ft Atkinson Wis.).

Specimens were resin embedded and sectioned undecalcified. Coronal sections (6 microns) were cut through the femoral head. Sections were stained with von Kossa to assess trabecular bone volume and structure. Fluorescent microscopy was used on unstained sections to image the fluorescent labels and assess bone formation.

One control rat died and was not replaced, leaving 23 pairs of proximal femora for analysis.

Results

Figure 3:
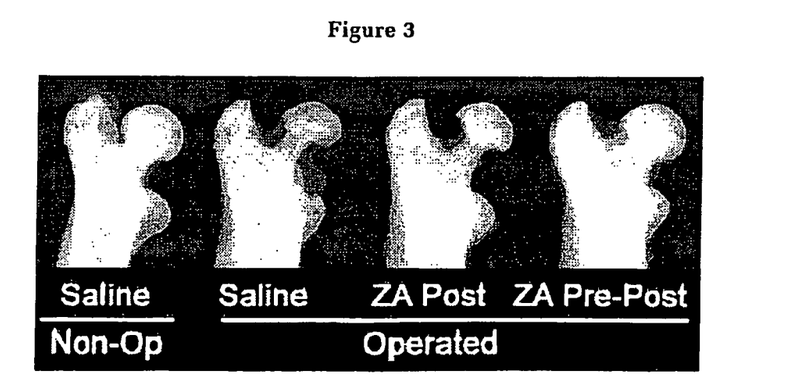
FIG. 3 is a set of representative radiographs of the proximal femurs of the rats of Example 1.

Representative radiographs are shown in FIG. 3. The entire set of x-rays of each proximal femur is given in FIG. 4. In this figure, the top row were in the saline group, the second row were in the post-treated group and the third row were in the pre and post-treated group. Right hips were operated on and left hips were not.

Figure 4:
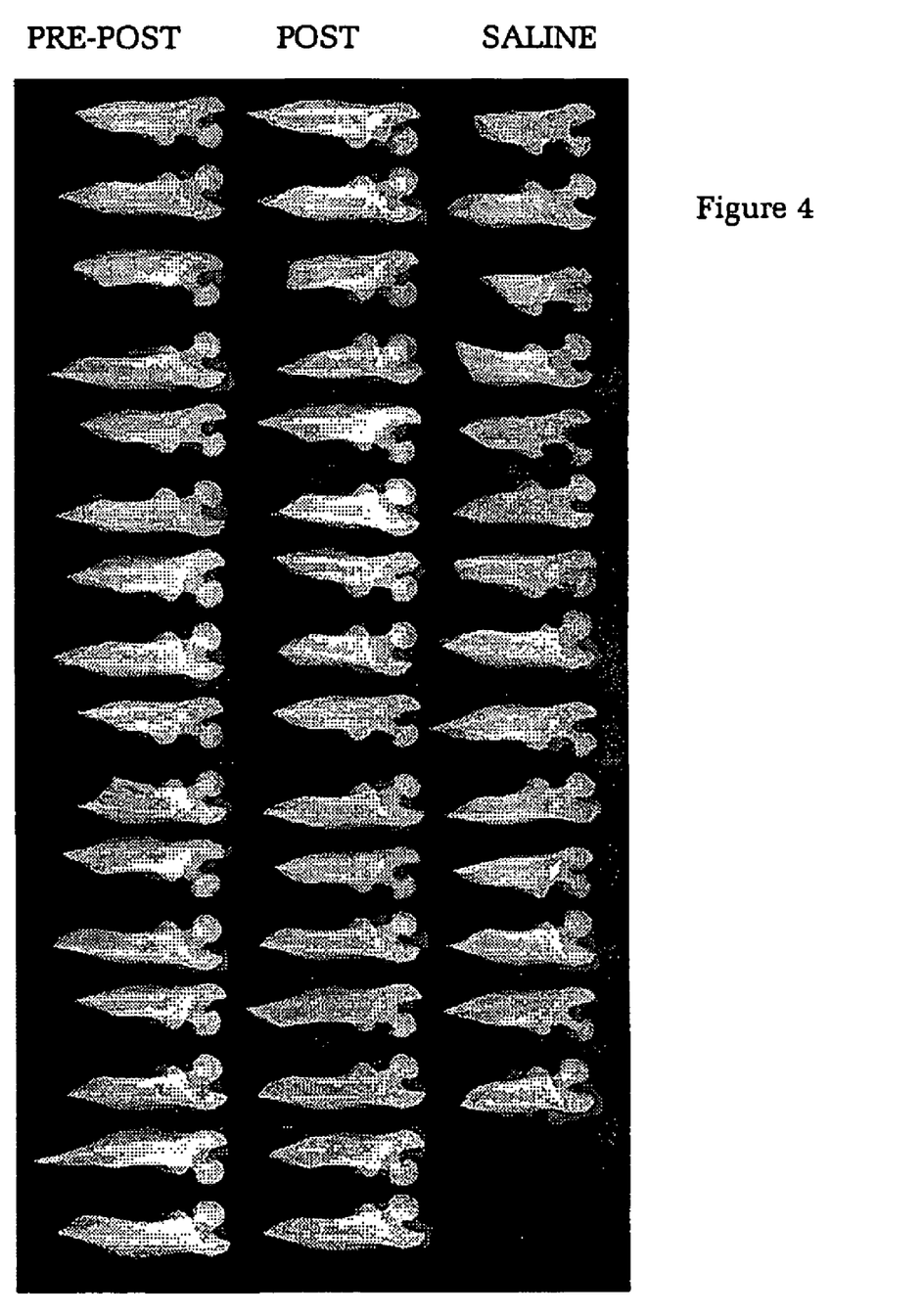
FIG. 4 is a set of X rays of the proximal femurs of each of the rats of Example 1.

Morphologically, the bony architecture was well preserved in the post treated group, apart from some femoral neck resorption. In the pre and post group, femoral heads were almost completely preserved.

The femoral heads in the saline group were smaller as a percentage of the non-operated side as measured by the Bioquant image analysis system (Table I). The femoral heads of the operated saline group were reduced to 63% of the contralateral (non-operated hip). This effect was significantly reduced when both treated groups were compared to the saline treated non-operated controls (p<0.01, ANOVA). The greatest preservation of the femoral head was in the pre-post treated group (85%), but the post treated group (79%) was still significantly better preserved than controls (p<0.01, t test).

TABLE I

Results

| | Non-Operated Control | Operated Control | Post-Treated | Pre- and Post |
|---|---|---|---|---|
| XR Head Area (% Contra) | — | 63 | 79 | 85 |
| BMD (g/cm²) | 0.11 | 0.07 | 0.11 | 0.12 |
| BMC (g) | 0.017 | 0.006 | 0.012 | 0.015 |

DEXA scans showed a significant increase (P<0.01, ANOVA) in femoral head BMD and BMC for treated over control groups, with preservation of values at or near non-operated controls (Table II). In our previous experiments we have found that strength correlates well with BMC, which was reduced to nearly one third in the saline group.

Figure 5:
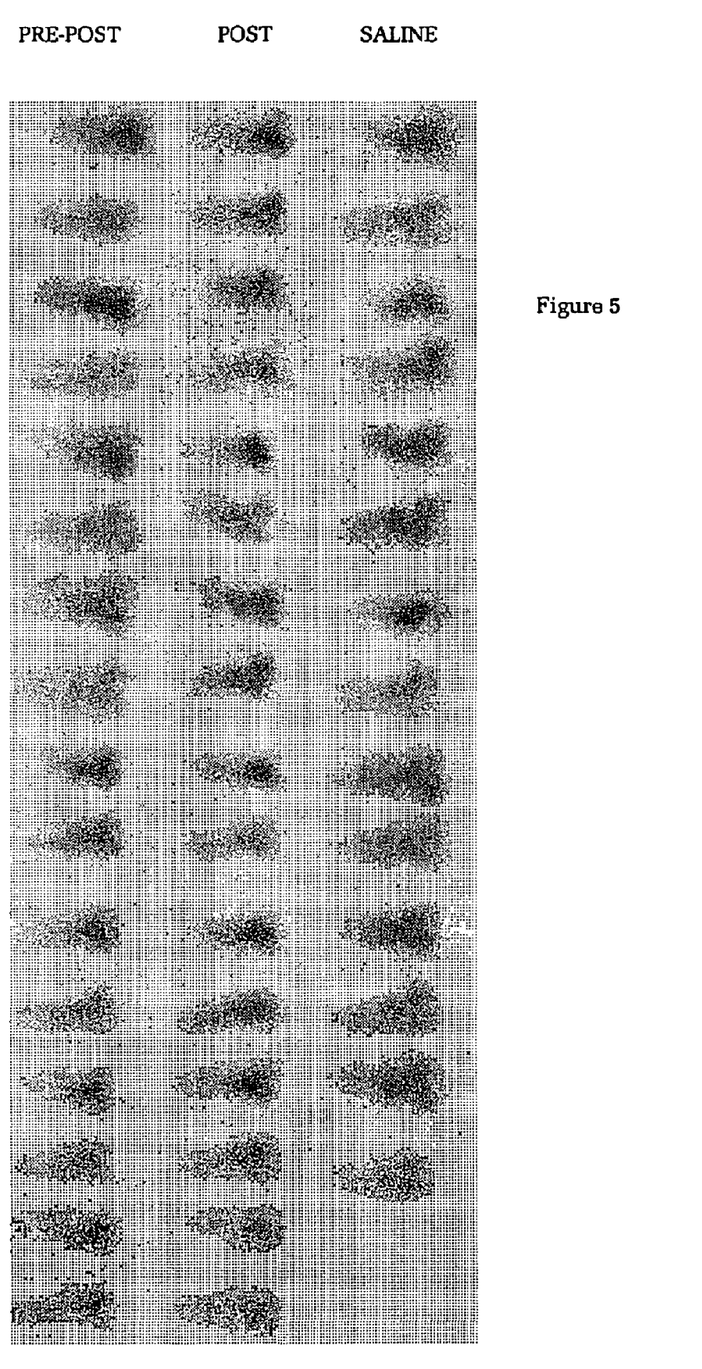
FIG. 5 is a set of TC 99 bone scans to show revascularisation of the proximal femurs of each of the rats of Example 1.

Bone scintigraphy showed complete revascularisation, the operated side producing increased uptake over the non-operated side in all cases as shown in FIG. 5. In this figure, the top row were in saline group, the second row were in the post-treated group and the third row were in the pre and post-treated group. Right hips were operated on and left were not.

Figure 6:
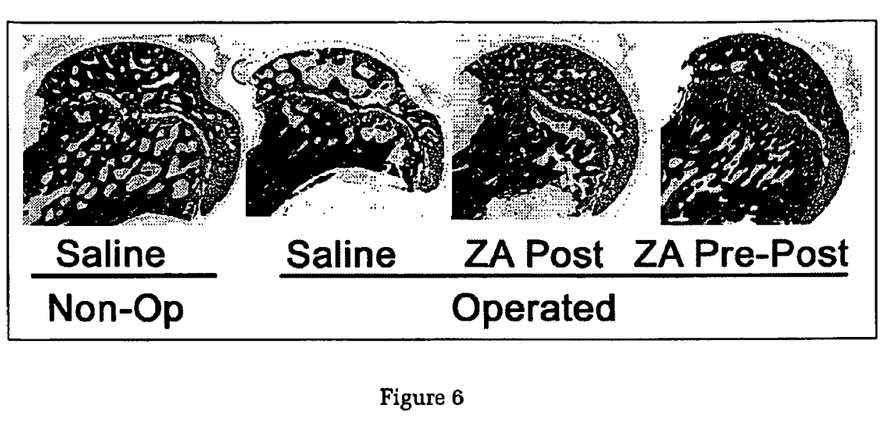
FIG. 6 is a set of Von Kossa undecalcified histology slides showing the preservation of bone architecture of the proximal femurs of the rats of Example 1.

Histology showed preservation of bone architecture in both treated groups, whereas the operated controls had resorbed much of the epiphysis, and it was broad and flat (FIG. 6).

Figure 7:
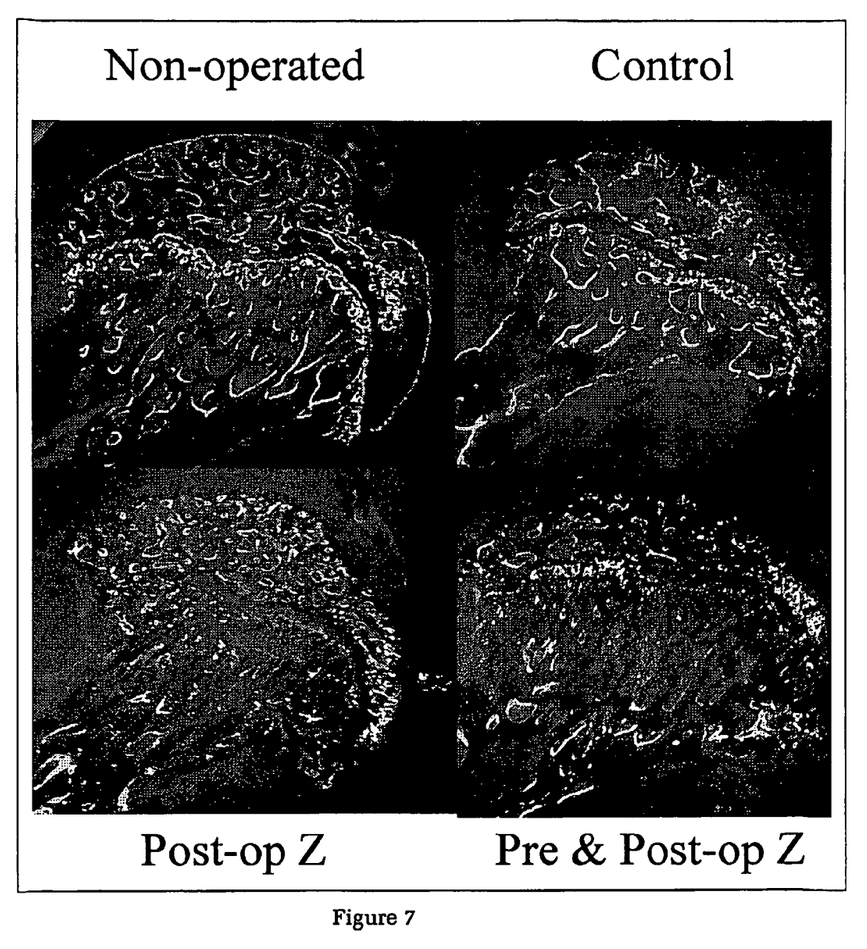
FIG. 7 is a set of toluidine blue histology slides showing the preservation of articular cartilage in the rats of Example 1.

There was also better preservation of articular cartilage in the treated groups (FIG. 7). Pre and post op rats showed thick articular cartilage with toluidine blue staining, consistent with further chondral growth but delayed ossification secondary to the avascular insult. Articular cartilage looked equivalent in post op treated and non-operated specimens, and worst in the controls where the cartilage was thin and had many areas of poor staining.

Figure 8:
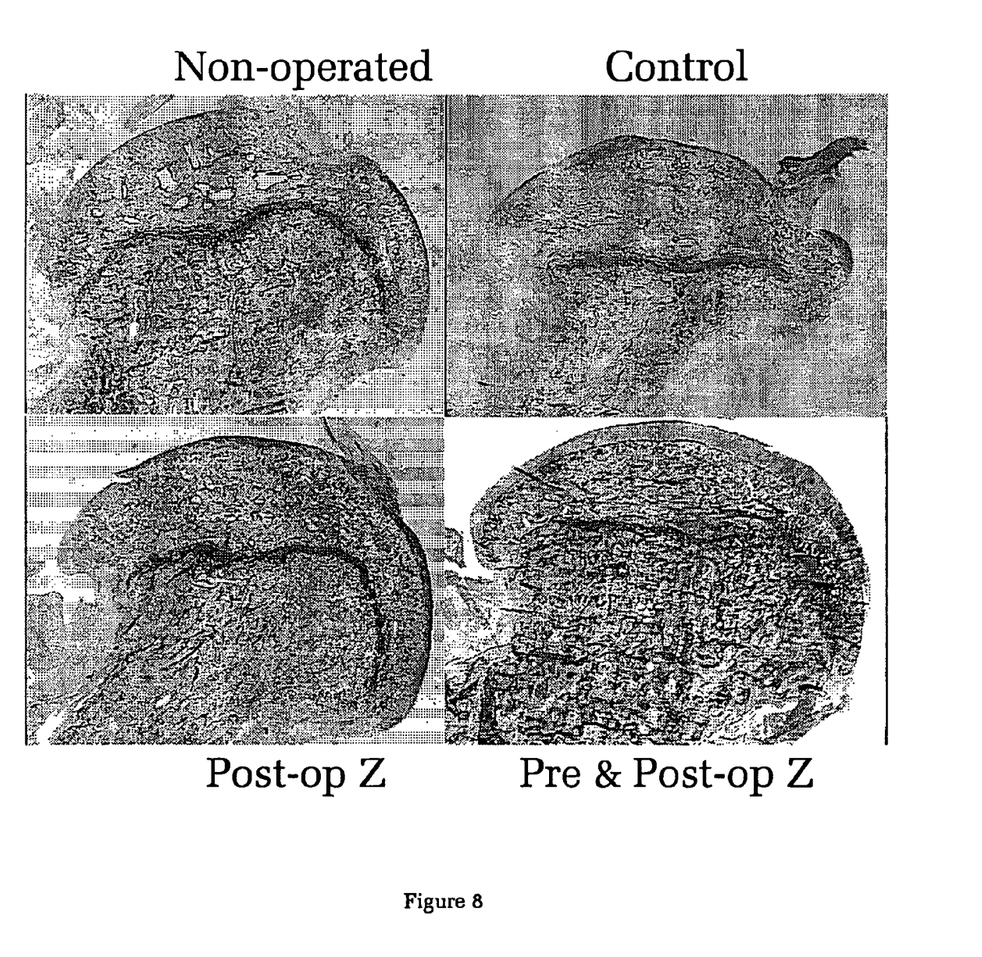
FIG. 8 is a set of fluorescent histology slides showing bone formation activity in the proximal femurs of the groups of rats in Example 1.

Tetracycline labelling showed bone formation had returned at 4 weeks in all groups (FIG. 8). Bone formation was florid in the operated controls, (top right) but had not repaired the massive resorption by six weeks. Bone formation in post-treated femoral heads was similar to non-operated controls (bottom left). Pre-post treated animals (bottom right) had definite but lesser amount of bone formation between weeks 4 and 5, with very few surfaces on which to form bone as it was so densely packed. There was no evidence of bone formation at the physis in the operated specimens.

Discussion

Administration of zoledronic acid reduced epiphyseal destruction (anti-resorptive effect) but also allowed new bone formation and mineralisation leading to a viable, preserved epiphysis. Articular cartilage preservation was also evident in treated groups.

The femoral necks were partially resorbed in the post treated group. It is assumed that this occurred in the week prior to zoledronic acid administration, as this was not present to the same degree in the pre and post group.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method of treating a patient with osteonecrosis, the method comprising:
   administering to the patient a drug consisting of at least one bisphosphonate or any pharmaceutically acceptable salt, hydrate or ester thereof.

2. The method of claim 1 wherein the at least one bisphosphonate or any pharmaceutically acceptable salt, hydrate or ester thereof is zoledronic acid or any pharmaceutically acceptable salt or ester thereof.

3. The method of claim 1 wherein the bisphosphonate is selected from the group consisting of pamidronate, alendronate, etidronate, clodronate, risedronate, tiludronate, ibandronate, incadronate, minodronate, olpadronate, neridronate, EB-1053 or any pharmaceutically acceptable salt, hydrate or ester thereof.

4. The method of claim 1, wherein said administering is intravenous.

5. The method of claim 1, wherein said administering is orally, subcutaneously, intramuscularly, transdermally, or topically.

6. The method of claim 1, wherein said administering is by local administration to a target treatment site.

7. The method of claim 6, wherein said administering is prior to, at the time of, or after, a core decompression procedure.

8. The method of claim 6, wherein said administering is administered prior to, at the time of, or after, a bone grafting procedure.

9. The method of claim 6, wherein said administering is prior to, at the time of, or after, a vascularised bone grafting procedure.

10. The method of claim 6, wherein said at least one bisphosphonate or any pharmaceutically acceptable salt, hydrate or ester thereof is administered together with a local delivery system.

11. The method of claim 10, wherein the local delivery system is a bone graft substitute or extender, or autogenous or allogenic bone graft.

12. The method of claim 2, wherein said administering is parenterally in a dose range of 0.25 mg to 12 mg in an adult patient or 0.005 mg/kg to 0.5 mg/kg in a child up to every three months.

13. The method of claim 2, wherein said administering is four-weekly, six-weekly or every two months.

14. The method of claim 2, wherein said administering is every twelve months.

15. The method of claim 2, wherein said administering is parenterally as a single dose.

16. The method of claim 3, wherein said at least one bisphosphonate or any pharmaceutically acceptable salt, hydrate or ester thereof is pamidronate or any pharmaceutically acceptable salt, hydrate or ester thereof, and wherein administering is parenterally in a dose range of 15 to 90 mg every one to six months in an adult patient or 0.25 mg/kg to 3.0 mg/kg every one to six months in a child.

17. The method of claim 3, wherein said at least one bisphosphonate or any pharmaceutically acceptable salt, hydrate or ester thereof is alendronate or any pharmaceutically acceptable salt, hydrate or ester thereof, and wherein said administering is orally in a dose range from 2.5 mg to 50 mg per day or 10 mg to 300 mg per week for an adult patient and from 0.05 mg/kg to 1.0 mg/kg per day or 0.2 mg/kg to 6.0 mg/kg per week in a child.

18. The method of claim 3 wherein said at least one bisphosphonate or any pharmaceutically acceptable salt, hydrate or ester thereof is alendronate or any pharmaceutically acceptable salt, hydrate or ester thereof, and said administering is parenterally in a dose range of 0.25 mg to 30 mg every one to three months, or as a single dose.

19. The method of claim 3, wherein said at least one bisphosphonate or any pharmaceutically acceptable salt, hydrate or ester thereof is risedronate or any pharmaceutically acceptable salt, hydrate or ester thereof administered orally in a dose range of 2.5 mg to 60 mg per day or 10 mg to 300 mg per week in an adult patient or 0.05 mg/kg to 1.0 mg/kg per day or 0.25 mg/kg to 7.0 mg/kg per week in a child.

20. The method of claim 3, wherein said at least one bisphosphonate or any pharmaceutically acceptable salt, hydrate or ester thereof is ibandronate or any pharmaceutically acceptable salt, hydrate or ester thereof administered parenterally in a dose range of 0.25 mg to 30 mg every one to three months, or as a single dose.

21. The method of claim 3, wherein said at least one bisphosphonate or any pharmaceutically acceptable salt, hydrate or ester thereof is ibandronate or any pharmaceutically acceptable salt, hydrate or ester thereof, and said administering is orally in a dose range of 2.5 mg to 30 mg per day, or 15 mg to 210 mg per week in an adult patient or 0.05 mg/kg to 0.5 mg/kg per day or 0.25 mg/kg to 2.5 mg/kg per week for a child.

22. The method of claim 3, wherein said at least one bisphosphonate or any pharmaceutically acceptable salt, hydrate or ester thereof is incadronate or any pharmaceutically acceptable salt, hydrate or ester thereof, and said administering is parenterally in a dose range of 0.25 mg to 30 mg in an adult patient or 0.005 mg/kg to 0.6 mg/kg in a child, wherein said dose is administered every one to three months, or as a single dose.

23. The method of claim 3, wherein said at least one bisphosphonate or any pharmaceutically acceptable salt, hydrate or ester thereof is minodronate or any pharmaceutically acceptable salt, hydrate or ester thereof, and said administering is parentally in a dose range of 0.25 mg to 30 mg every one to three months, or as a single dose.

24. The method of claim 3, wherein said at least one bisphosphonate or any pharmaceutically acceptable salt, hydrate or ester thereof is clodronate or any pharmaceutically acceptable salt, hydrate or ester thereof, and said administering is orally in a dose range of 400 mg to 2400 mg per day or administered intravenously in dose ranges from 150 mg to 300 mg repeated daily for 2 to 5 days.

25. The method of claim 3, wherein said at least one bisphosphonate or any pharmaceutically acceptable salt, hydrate or ester thereof is etidronate or any pharmaceutically acceptable salt, hydrate or ester thereof, and said administering is orally in a dose range of 100 mg to 400 mg per day in an adult or 5 mg to 20 mg/kg per day in a child.

26. The method of claim 3, wherein said at least one bisphosphonate or any pharmaceutically acceptable salt, hydrate or ester thereof is tiludronate or any pharmaceutically acceptable salt, hydrate or ester thereof, and said administering is orally in a dose of 400 mg per day in an adult or 5 mg to 20 mg/kg per day in a child.

27. The method of claim 3, wherein said at least one bisphosphonate or any pharmaceutically acceptable salt, hydrate or ester thereof is olpadronate or any pharmaceutically acceptable salt, hydrate or ester thereof, and wherein said administering is orally in a dose range of 50 mg to 400 mg per day in an adult or 1 mg/kg to 10 mg/kg in a child or administered intravenously every one to three months in dose ranges from 1 mg to 20 mg in an adult or 0.1 mg/kg to 0.5 mg/kg in a child.

28. The method of claim 3, wherein said at least one bisphosphonate or any pharmaceutically acceptable salt, hydrate or ester thereof is neridronate or any pharmaceutically acceptable salt, hydrate or ester thereof, and said administering is parenterally in a dose range of 10 mg to 100 mg in an adult.

* * * * *